United States Patent
Prasad

(10) Patent No.: US 12,246,079 B2
(45) Date of Patent: Mar. 11, 2025

(54) BISACURONE COMPOSITION AND METHOD OF SKIN WHITENING

(71) Applicant: Vidya Herbs, Inc., Fullerton, CA (US)

(72) Inventor: Kodimule Shyam Prasad, Bangalore (IN)

(73) Assignee: Vidya Herbs, Inc., Red Bank, NJ (US)

( * ) Notice: Subject to any disclaimer, the term of this patent is extended or adjusted under 35 U.S.C. 154(b) by 222 days.

(21) Appl. No.: 16/785,226

(22) Filed: Feb. 7, 2020

(65) Prior Publication Data

US 2020/0253847 A1     Aug. 13, 2020

Related U.S. Application Data

(60) Provisional application No. 62/802,601, filed on Feb. 7, 2019.

(51) Int. Cl.
*A61K 8/35*     (2006.01)
*A61K 8/9794*     (2017.01)
*A61Q 19/02*     (2006.01)

(52) U.S. Cl.
CPC .............. *A61K 8/35* (2013.01); *A61K 8/9794* (2017.08); *A61Q 19/02* (2013.01)

(58) Field of Classification Search
None
See application file for complete search history.

(56) References Cited

U.S. PATENT DOCUMENTS

2004/0028751 A1\*   2/2004   Mae .................... A61K 36/9066
                                             424/684
2010/0311668 A1\*   12/2010   Farwick ............... A61K 31/716
                                             514/18.8

FOREIGN PATENT DOCUMENTS

JP          02017081874 A   \*   5/2017

OTHER PUBLICATIONS

Sun et al. Bisacurone Inhibits Adhesion of Inflammatory Monocytes or Cancer Cells to Endothelial Cells Through Down-Regulation of VCAM-1 Expression, International Immunopharmacology 8, 1272-1281 (2008) (Year: 2008).\*

\* cited by examiner

*Primary Examiner* — David J Blanchard
*Assistant Examiner* — Sarah J Chickos
(74) *Attorney, Agent, or Firm* — TMB Law; Timothy M. Brown

(57) ABSTRACT

Disclosed is a composition comprising bisacurone. The composition finds use in treating the skin, including skin whitening applications. The composition can be obtained from an extract of turmeric rhizome.

12 Claims, 4 Drawing Sheets

BISACURONE COMPOSITION AND METHOD OF SKIN WHITENING

CROSS-REFERENCE TO RELATED APPLICATIONS

This application claims the benefit of Provisional Application No. 62/802,601 filed Feb. 7, 2019, the entire contents of which are incorporated herein by reference for all purposes.

FIELD OF INVENTION

The invention generally relates to cosmetics. More particularly, the invention relates to a composition containing bisacurone and a method of its use and manufacture in skin whitening.

BACKGROUND OF THE INVENTION

With aging, an individual may experience serious undesirable effects on the visual appearance of the skin due to environmental factors, oxidative stress, aging, and malnutrition. These deleterious effects on the skin include loss of elasticity, wrinkle formation, hyperpigmentation, dark age spots, dullness, loss of firmness, and a less attractive surface texture.

Skin pigmentation has been a concern of individuals for many years. In particular, the ability to remove or lessen the appearance of hyperpigmentation, such as found in melasma, age spots, liver spots, freckles, or aging skin generally, is of interest to individuals desiring a uniform skin color and an attractive complexion. In addition, achieving less pigmented skin is desired by some. There are also disorders or conditions of hypopigmentation (i.e., areas of less dark skin color than the surrounding or adjacent, normal pigmented skin) that are desirable to treat.

Many compositions and methods have been proposed to accomplish skin whitening. For example, arbutin, kojic acid, hydroquinone, retinoids, and other chemical compounds have been used for whitening. However, many of these compounds have been found to irritate the skin and are therefore undesirable for use. Also, precise application of these compounds may be necessary in order to achieve the desired result and avoid a distinct line of demarcation between the areas of skin to which such previous compositions have been applied.

Accordingly, there is a need for a composition which allows skin depigmentation without irritation or the need for a precise, uniform application. The compositions and methods of the present invention address these long felt needs in the art.

SUMMARY OF THE INVENTION

The inventor surprisingly discovered a composition comprising bisacurone that can have efficacy in whitening the skin without the undesirable side effects of known skin whitening compositions and their associated methods.

It is therefore an object of the invention to provide a skin whitening composition that comprises bisacurone and does not have the side effects associated with known skin whitening compositions.

It is a further object of the invention to provide a method comprising administering the composition to a patient in need of skin whitening.

These and other objects will become apparent to one skilled in the art in view of the following description and examples.

DETAILED DESCRIPTION

Figure 1A:
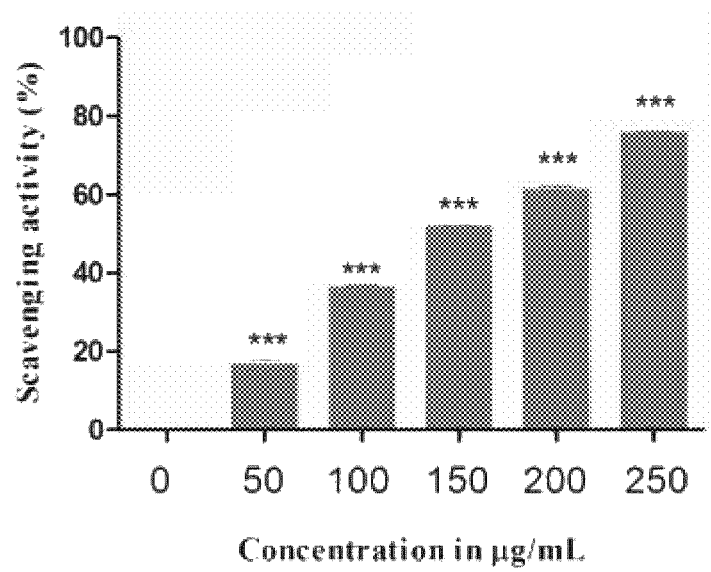
FIGS. 1A and 1B show the DPPH and nitric oxide radical scavenging activities of an embodiment of the inventive composition.

The following detailed description is intended to describe some, but not necessarily all, examples or embodiments of the invention. As will be realized, the invention is capable of modification in various obvious respects, all without departing from the invention. Accordingly, the described and exemplified embodiments are to be considered in all respects illustrative and not restrictive.

Disclosed is a composition comprising bisacurone and methods of its use and manufacture for skin whitening and other cosmetic uses. In some aspects, the composition comprises purified bisacurone. As used herein, the term "purified" means the referenced material is isolated using chromatography, distillation, extractions, or similar techniques and has greater than 60%, 70%, 80%, 90%, or 95% purity.

In some embodiments, the invention provides a composition consisting essentially of bisacurone. As used herein, the phrase "consisting essentially of" limits the scope of a claim to the specified elements or method steps, plus those that do not materially affect the basis and novel characteristic(s) of the claimed subject matter. For example, the composition can consist essentially of bisacurone, and include one or more excipients for facilitating the administration of the bisacurone to a patient, and/or improve its stability, storage, and/or handling properties. The composition can consist essentially of bisacurone, and exclude those agents known in the art at the time of filing the present disclosure, to have efficacy in, or contribute to, whitening the skin.

The composition can comprise one or more excipients. The invention can be practiced with any excipient that permits the composition to have its intended effect of whitening the skin. Suitable excipients for use with the invention include, but are not limited to, carriers, binders, fillers, flow aids/glidents, disintegrants, lubricants, stabilizers, surfactants, and the like. The excipient can be one or more of those disclosed in the following references, the entire disclosures of which are incorporated herein by reference for all purpose: Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999).

In some embodiments, the composition can comprise an extract of turmeric (Curcuma longa) that contains bisacurone. The extract can be obtained from any part of the turmeric plant, or combination of turmeric plant parts, that is capable of providing a composition that comprises bisacurone and is effective in whitening the skin. The extract can be obtained from turmeric rhizomes. Suitable extraction techniques include, but are not limited to, extrusion, solvent extraction, or a combination thereof. Suitable solvents for providing an extract for the composition include, but are not limited to, aqueous solvents, alcohol-based solvents, supercritical fluids, polar organic solvents (such as acetone and methylethyl ketone), or combinations thereof. Non-limiting examples of alcohol-based solvents include, but are not limited to, ethanol, isopropyl alcohol, methanol, and combinations thereof. The supercritical fluid can be, but is not necessarily limited to, carbon dioxide.

The composition can further comprise one or more vitamins, minerals, amino acids, proteins, carbohydrates, lipids, fatty acids, food, beverage, nutritional or dietary supplements, excipients, pharmaceutically acceptable carriers, bulking agents, binding agents, caffeine, flavorings, sweeteners, preservatives, or combinations thereof. In at least one aspect of the invention, the composition is provided and/or manufactured in bulk. The composition can be provided in bulk for the manufacture of foods, nutritional supplements, nutraceuticals, dietary supplements, cosmetics, and/or food supplements for whitening the skin. Bulk quantities of the composition can be packaged, stored and/or distributed in packaging such as drums, bags, boxes, containers and the like. Such packaging can be configured to prevent or inhibit the oxidation of one or more active ingredients in the composition.

In at least one embodiment, the invention is provided as a cosmetic composition. The term "cosmetics" includes medicated cosmetics such as dermatological preparations, ointments, solutions, creams, emulsions, toners, lotions, gels, essences, foundations, pack masks, lipsticks, sticks, bath preparations, and the like. The cosmetic form can encompass a broad range of formulation types such as a solution solubilized formula, powders, powder dispersions, oily solutions, gels, ointments, aerosols, water-in-oil, water-in-oil-in-solid types, and the like.

The cosmetic composition according to this invention can be in the form of hair shampoos, hair lotions, foam baths, shower bath creams, soaps, gels, lotions, alcoholic and aqueous/alcoholic solutions, emulsions, wax/fat masses, stick preparations, powders, or ointments. These compositions can also comprise further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, hydrotropes, solubilizers, preservatives, perfume oils, dyes and the like. The inventive cosmetic composition may further comprise at least one surfactant.

In at least one embodiment, the invention provides a method for whitening the skin in which a composition according to the invention is administered to a patient. As used herein, the term "whitening" means a change in the color of skin to a color which is lighter compared to the state of the skin before the administration of a composition according to the invention. The term "whitening" encompasses the lightening, removal or reduction of pigmentation, including spots and/or of freckles of hyperpigmentation which might be caused by sun exposure. In at least one aspect, administering the composition prevents or inhibits the darkening of the skin. In at least some embodiments, the patient is human.

The term "reduction" as used in connection with pigmentation or hyperpigmentation indicates that the amount of pigments, including spots, freckles, and/or liver spots, preferably melanin in the skin, is reduced compared to the skin before administering a composition according to the present invention.

The patient can have a pigmentation disorder in which the pigmentation of the skin presents an undesired skin appearance. The pigmentation disorder can be a skin color that is darker than desired by the patient, or any hyperpigmentation disorder in which areas of darker skin are surrounded by lighter areas of skin, including without limitation liver spots, sun spots, age spots, freckles, melasma, lentigo, hypopigmentation, and hyperpigmentation such as post-inflammatory hyperpigmentation. In some aspects, the skin disorder is characterized by an area of lighter skin surround by darker skin, such as vitiligo, for example. Administration of the composition can decrease the contrast of darker skin against lighter skin by reducing pigmentation in the darker skin.

The composition can be administered according to any route capable of lightening the skin of the patient. Suitable administration routes include, but are not limited to, auricular, buccal, conjunctival, cutaneous, dental, endocervical, endosinusal, endotracheal, enteral, epidural, extra-amniotic, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal dental, intracoronary, intracorporus cavernosum, intradermal, intradiscal, intraductal, intraduodenal, intradural, intraepidermal, intraesophageal, intragastric, intravaginal, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parentera, percutaneous, periarticular, peridural, perineural, periodontal, rectal, inhalation, retrobulbar, soft tissue, subarachnoid, subconjunctival, subcutaneous, sublingual, submucosal, topical, transdermal, transmucosal, transplacental, transtracheal, transtympanic, ureteral, urethral, vaginal, or combinations thereof. The composition can be administered by irrigation, drip, infusion, or topically by a dressing, patch, tape, or bandage that is in contact with the composition.

The composition can be used alone or together with other known agents used in the technical field of the present invention. Accordingly, the composition can be used together with at least one member selected from the group consisting of kojic acid, hydroquinone, alpha- and beta-arbutin, other hydroquinone glycosides, deoxyarbutin, ferulic acid, diacetyl-boldine, azelaic acid, octadecenedioic acid, linoleic acid, conjugated linoleic acid, alpha-lipoic acid, glutathione and derivatives, undecylenoyl-phenylalanine, vitamin C and derivatives as magnesium L-ascorbylphosphate, niacinamide, 4-n-butyl-resorcinol, alpha- and beta-hydroxy acids, ellagic acid, resveratrol, *Morus alba* extracts, glabridin and liquorice extracts, imperatorin and isoimperatorin and *Angelica dahurica* extracts, centaureidin and Yarrow extracts, *Bellis perennis* extracts, *Phyllanthus emblica* extracts, water cress extracts, *Veratum nigrum* extracts, *Sophora flavescens* extracts, ascomycete-derived melanin-degrading enzyme, acetoxysinapinic acid and 2-(4-hydroxyphenoxy)propionic acid.

The inventor surprisingly discovered that the composition of the invention can have efficacy in the treatment of melanoma. Accordingly, the invention further provides a method of treating melanoma in a patient in need thereof, wherein a composition as disclosed herein is administered to the patient. The composition can be administered according to the administration routes disclosed herein. In a non-limiting embodiment, the composition is administered to a melanoma lesion on the skin of the patient. The composition can be a turmeric rhizome extract that comprises bisacurone. Treating melanoma with the composition can include reducing or inhibiting the progression or symptoms of the disease. Treating melanoma with the composition can reduce melanoma cell viability and/or inhibit the replication of melanoma cells, for example.

EXAMPLES

The present invention is exemplified by the following examples. Example 1 describes the evaluation of in vitro antioxidant activities of the inventive composition. Example 2 illustrates the inhibitory effect of the inventive composition on mushroom tyrosinase enzyme activity in vitro. Example 3 describes the effect of the inventive composition on melanogenesis in B16F10 murine melanoma cells. References to the composition and the term "Turcuron" in the following examples and drawings refer to an embodiment of the inventive composition that is turmeric rhizome extract comprising bisacurone.

Example 1—In Vitro Antioxidant Activities

DPPH Radical Scavenging Assay

DPPH free radical scavenging activity of the composition was carried out by adopting the protocol described by Braca et al., 2001. Briefly, 1 ml of 0.004% DPPH solution in ethanol were mixed with 1 ml of the composition at different concentrations (50-250 µg/mL), the reaction mixture was mixed well and allowed to reach a stable state at room temperature for 30 min and the absorbance was read at 515 nm.

Nitric Oxide (NO) Scavenging Assay

Nitric oxide generated from sodium nitroprusside was measured by the Griess reagent by the method of Marcocci et al. (1994). Various concentrations of the composition (100-1000 µg/mL) and sodium nitroprusside (5 mM) were taken in test tube in a final volume of 3 ml PBS and reaction mixture were incubated at 25° C. for 150 min. After incubation, 0.5 ml of reaction mixture were removed and diluted with 0.5 ml of Griess reagent (1% sulphanilamide, 2% o-phosphoric acid and 0.1% naphthyl ethylenediamine dihydrochloride). The absorbance of the chromophore formed was read at 546 nm. The inhibition of nitric oxide generation was calculated by comparing the absorbance values of control with that of treatments.

Figure 1B:
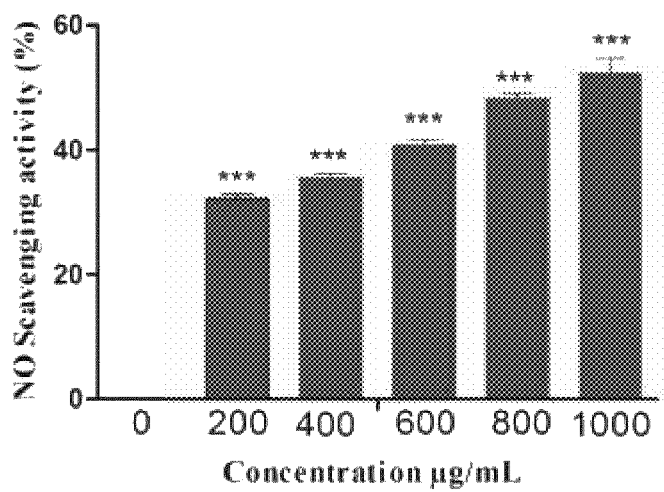

Antioxidant activity of the composition was determined by DPPH and NO assay. Interestingly the composition inhibited DPPH radical scavenging activity in dose dependent manner. The maximum DPPH scavenging activity at a value of 75.89% at 250 ng/mL and calculated IC50 value was found to be 0.155 mg/Ml (FIG. 1A). Further, the composition dose dependently decreased nitric oxide generation. Nitric oxides are very unstable; it reacts with oxygen to produce stable nitrates and nitrites through intermediates which is determined by Griess reagent. The amount of nitrous acid decreases indicates the amount of scavenging. The calculated IC50 value was found to be 0.928 mg/mL. The findings (FIG. 1B) indicate that the composition has strong DPPH radical scavenging and moderate NO scavenging activity.

Example 2—Effect on Mushroom Tyrosinase Enzyme Activity In Vitro

This assay was performed using the method described by Curto et al. (1999) and Nerya et al. (2003). The composition was dissolved in phosphate buffer to a final concentration of 10 mg/ml. This stock solution was further diluted in 50 mM potassium phosphate buffer (pH 6.5). 70 µl of each concentration was combined with 30 µl of tyrosinase (333 Units/ml in phosphate buffer) in triplicate. After incubation at room temperature for 5 minutes, 110 µl of substrate (2 mM L-L-DOPA) was added to each well. Final concentrations of the composition ranged from 100 to 500 µg/ml. Incubation commenced for 30 minutes at room temperature. Optical densities of the wells were then determined at 492 nm with the Multiscan Ex plate reader (Thermofischer). All the experiments were repeated thrice.

Figure 2:
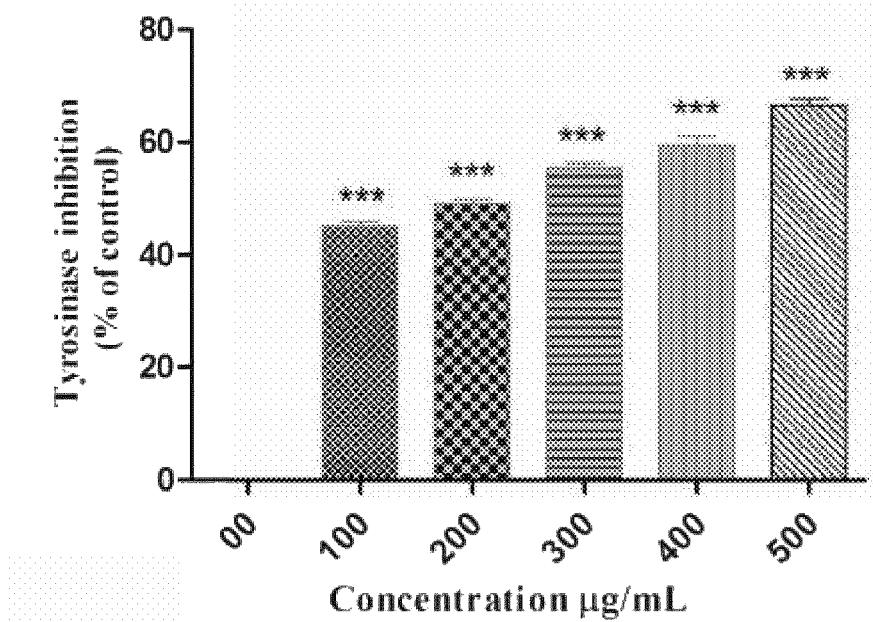
FIG. 2 shows the tyrosinase inhibitory activity of an embodiment of the inventive composition using L-DOPA as a substrate. All assays have been demonstrated in triplicate and error bars represent S.E.M. P value represents *$P<0.05$; $P<0.01$; *$P<0.001$.

Tyrosinase is an enzyme that is involved in the rate-limiting step for the control of melanin production. Therefore, the inhibition of tyrosinase activity tends to induce skin whitening due to a reduction of melanin synthesis. When the tyrosinase enzyme was incubated with the composition, interestingly it could inhibit tyrosinase activity in a concentration dependent manner. The composition strongly inhibits mushroom tyrosinase activity with an IC50 value of 204.71 µg/mL (FIG. 2).

Example 3—Effect on Melanogenesis in B16F10 Murine Melanoma Cells

Cell Culture

B16F10 cells (obtained from National Centre for Cell Sciences (NCCS), Pune, India) were cultured in Dulbecco's Modified Eagle's Medium (DMEM; Sigma Aldrich Co, St Louis, USA) with 10% fetal bovine serum (FBS) and penicillin/streptomycin (100 IU.50 Pg ml-1) in a humidified atmosphere of 5% $CO_2$ at 37° C. The cells were cultured in 6-well plates for melanin quantification and enzyme activity assays.

Cell Viability

Cell survival was quantified by a colorimetric assay that used 3-(4, 5-dimethylthiazol-2-yl)-2, 5-diphenyltetrazolium bromide (MTT) and that measured mitochondrial activity in viable cells. This method is based on the conversion of MTT (Sigma) to MTT formazan crystals by a mitochondrial enzyme, as previously described (Tada et al 1986)

Determination of Melanogenesis in B16F10 Cells

Determination of melanin content of cells was done using a modification of the method of Bilodeau et al (Bilodeau et al 2001). In the present study, the amount of melanin was used as an index of melanogenesis. B16 F10 cells ($5\times10^4$) were transferred to 24-well dishes and incubated in the presence or absence of 100 nM α-MSH. Cells were then incubated for 24 h with different concentration of the composition. After washing twice with PBS, samples were dissolved in 100 µl of 1N NaOH. The samples were then incubated at 60° C. for 1 h and mixed to solubilize the melanin. Absorbance at 405 nm was compared with a standard curve of synthetic melanin.

Assay of Cellular Tyrosinase Activity

Tyrosinase activity was estimated by measuring the rate of L-DOPA oxidation (Kim et al 2002). Cells were plated in 6-well dishes at a density of $5\times10^4$ cells. B16 cells were incubated in the presence or absence of 5 µM α-MSH, and then treated for 48 h with two different concentrations of the composition. Cells were washed and lysed in 100 µl of 50 mM sodium phosphate buffer (pH 6.5) containing 1% Triton X-100 (Sigma) and 0.1 mM PMSF (phenylmethylsulfonyl fluoride), and then frozen at −80° C. for 30 min. After thawing and mixing, cellular extracts were clarified by centrifugation at 12,000 rpm for 30 min at 4° C. And 50 µl sample of the supernatant and 50 µl of L-DOPA (2 mM) were placed in a 96-well plate, and the absorbance at 492 nm was read every 10 min for 1 h at 37° C. using an ELISA plate reader thermoscan EX.

Western Blotting

B16F10 cells were treated with 200 and 400 µg of the composition with 5 µM α-MSH for 48 h. Whole cell lysates (100 µg protein each) were resolved by 10% SDS-PAGE, transferred to a polyvinylidene difluoride membrane and probed with primary antibodies specific to, tyrosinase. After washing, membranes were incubated with horseradish peroxidise conjugated secondary antibody (Santa Cruz Biotechnology). Immunodetection was performed using a chemiluminescence method and then normalized with β-actin.

Figure 3:
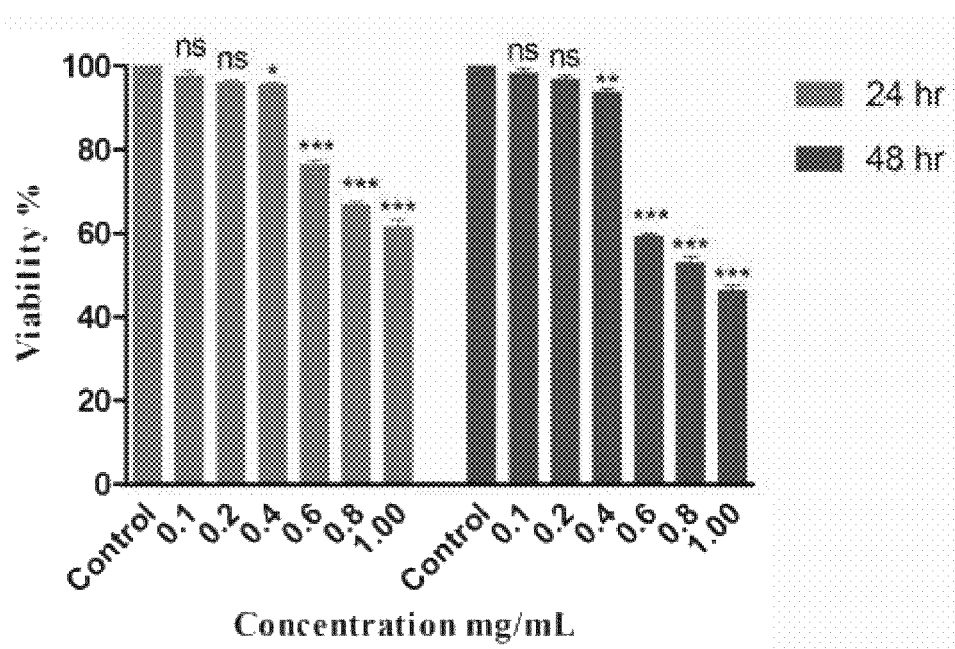
FIG. 3 shows the cytotoxicity of an embodiment of the inventive composition on B16F10 murine melanoma cells using MTT assay. The cells were treated with or without various concentrations of the composition (0.2-1.0 mg/mL) for 24 and 48 h. The cell viability was determined using MTT assay. All assays were performed in triplicate and error bars represent S.E.M. P value represents *$P<0.05$; $P<0.01$; *$P<0.001$.

MTT assay was used to examine the effect of the composition on cell viability of B16F10 cells. B16F10 cells were treated with various concentrations (0.1-1.0 mg/mL) of the composition for 24 and 48 h (FIG. 3). The result indicates that, cell viability was not inhibited by low concentration whereas the higher concentrations of the composition significantly inhibited the cell viability. Cell viability was still about 93% at the concentration of 0.4 mg/mL after 48 h (FIG. 3). Further experiments using 0.1, 0.2 and 0.4 mg/mL of the composition were used.

Figure 4A:
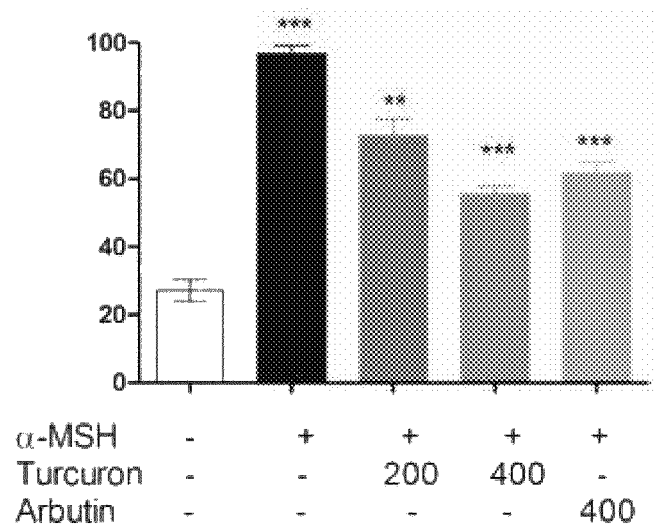
FIG. 4A shows the effect of an embodiment of the inventive composition on melanin content in α-MSH-stimulated B16F10 murine melanoma cells.

In order to assess the anti-melanogenesis activity of the composition, the melanin content was measured in both α-MSH-untreated and α-MSH-treated B16F10 cells. The cells were treated with/without α-MSH, followed by treatment with the composition at doses of 100, 200 and 400 µg/Ml (FIG. 4A). The results demonstrated composition treatment markedly inhibited melanin synthesis in a dose-dependent manner compared to α-MSH alone treated B16F10 cells. At 200 and 400 µg the melanin content was decreased by 24.02 and 41.46% respectively where as standard arbutin showed 35.96% decrease at 400 µg it is very clear that the composition has potent anti-melanogenesis property.

Figure 4B:
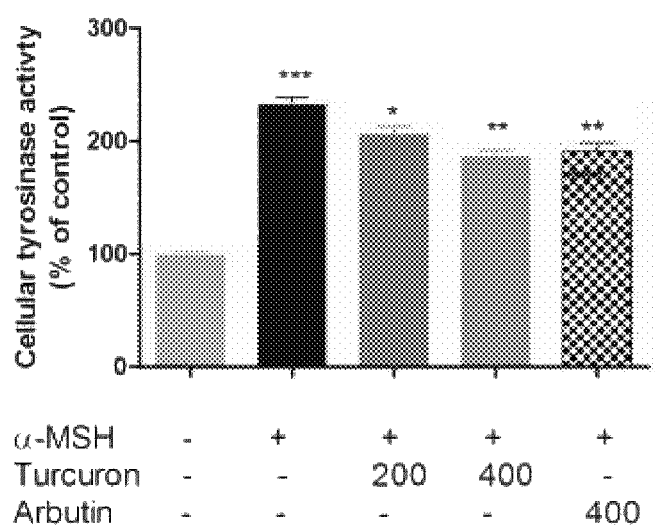
FIG. 4B shows the effect of an embodiment of the inventive composition on cellular tyrosinase activity in α-MSH-stimulated B16F10 murine melanoma cells. Experiments were performed in triplicate, and results are presented as means±SE. *$p<0.05$, **$p<0.01$

Since tyrosinase is the rate-limiting enzyme of melanin synthesis, we measured the inhibitory effect of the composition on cellular tyrosinase activity in B16F10 cells. The composition significantly inhibited Tyrosinase activity by 26.89%, and 46.63% respectively. The melanin content and tyrosinase activities of the composition at 0.2 and 0.4 mg/mL were similar to those of 400 µg/mL arbutin, showing that the composition displays a dose-dependent anti-melano cellular tyrosinase activity (FIG. 4B).

Figure 5:
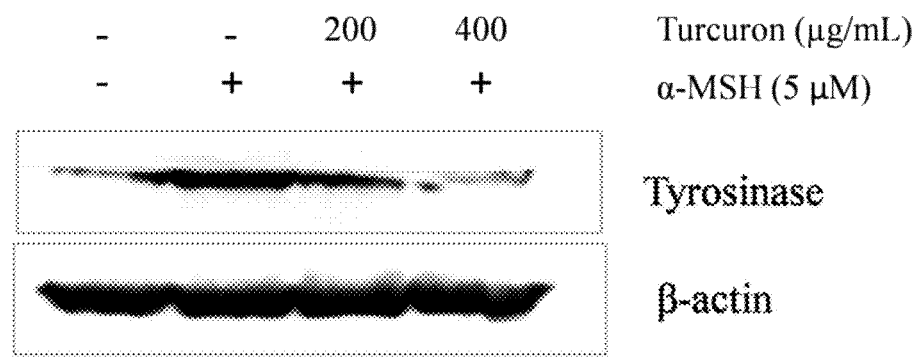
FIG. 5 shows the effect of an embodiment of the inventive composition on expression of melanogenesis-related protein tyrosinase in α-MSH-stimulated B1610 cells using Western blot analysis.

To determine whether the inhibitory activity of the composition is associated with expression levels of melanogenesis-related proteins Western blot analysis was carried out. Cells were exposed to α-MSH with or without composition treatment. α-MSH treatment significantly induced tyrosinase protein expression levels in B16F10 cells which were reduced in dose-dependent manner compared to α-MSH treated cells (FIG. 5). The data suggest that the inhibition of melanogenesis is associated with the down regulation of tyrosinase.

REFERENCES

Dweck A C. Botanicals—Research of actives. Cosmet Toilet 1996; 111: 45-57.
Aburjai T, Natsheh F M. Plants used in cosmetics. Phytother Res 2003; 17: 987-1000.
Dubey N K, Kumar R, Tripathi P. Global promotion of herbal medicine: India's opportunity. Curr Sci 2004; 86: 37-41.
Durej a H, Kaushik D, Gupta M, Kumar V, Lather V. Cosmeceuticals: An emerging concept. Indian J Pharm 2005; 37: 155-159.
Chaudhari P M, Kawade P V, Funne S M. Cosmeceuticals-A review. Int J Pharm Technol 2011; 3: 774-798.
Kaur G, Jabbar Z, Athar M, Alam M S. *Punica granatum* (pomegranate) flower extract possesses potent antioxidant activity and abrogates Fe-NTA induced hepatotoxicity in mice. Food Chem Toxicol 2006; 44: 984-993.
Marquele-Oliveira F, Fonseca Y M, de Freitas O, Fonseca M J V. Development of topical functionalized formulations added with propolis extract: Stability, cutaneous absorption and in vivo studies. Int J Pharm 2007; 342: 40-48.
Burke K E. Photodamage of the skin: Protection and reversal with topical antioxidants. J Cosmet Dermatol 2004; 3: 149-155.
Lall N, Kishore N. Are plants used for skin care in south africa fully explored? J Ethnopharmacol 2014; 153: 61-84.
Grimes P, Nordlund J J, Pandya A G, Taylor S, Rendon M, Ortonne J P. Increasing our understanding of pigmentary disorders. J Am Acad Dermatol 2006; 54: S255-S261.

The invention claimed is:

1. A method of whitening skin, comprising:
   a) administering to a subject in need thereof a composition consisting essentially of bisacurone, wherein said composition is free of any other skin whitening agents;
   b) wherein administering said composition whitens the skin of said subject.

2. The method of claim 1, wherein said bisacurone is isolated.

3. The method of claim 1, wherein said composition is administered systemically.

4. The method of claim 1, wherein said composition is administered orally.

5. The method of claim 1, wherein said composition is administered topically.

6. The method of claim 1, wherein said composition is in an administration form selected from an ointment, solution, cream, emulsion, lotion, gel, foundation, pack mask, lipstick, stick, bath preparation, powder, powder dispersions, aerosol, water-in-oil, oil, and combinations thereof.

7. The method of claim 1, wherein said administering step further comprises administering at least one additional agent selected from L-alanine, glycine, L-isoleucine, L-leucine, hydroquinone, 4-(1-phenylethyl) 1,3-benzenediol, arbutin, bearberry leaf extract, kojic acid, oxyresveratrol, gnetol, a melanosome transfer inhibitor, and an a-MSH antagonist.

8. The method of claim 1, wherein said subject has a skin disorder selected from undesirably dark skin, liver spots, sun spots, age spots, freckles, melasma, lentigo, vitiligo, hypopigmentation, hyperpigmentation, post-inflammatory hyperpigmentation, and combinations thereof.

9. The method of claim 1, wherein said subject is human.

10. The method of claim 1, wherein said administering step further comprises administering at least one of a skin moisturization agent and a skin rejuvenation agent.

11. The method of claim 10, wherein said skin rejuvenation agent is selected from ascorbic acid, vitamin E, jojoba oil, shea butter, human fibroblast lysate, retinoic acid, retinol, and-derivatives thereof.

12. The method of claim 1, wherein said bisacurone is contained within an extract of turmeric rhizome.

\* \* \* \* \*